US012721516B2

(12) United States Patent
Hallen

(10) Patent No.: US 12,721,516 B2
(45) Date of Patent: Sep. 1, 2026

(54) VITREOUS FLOATER CHARACTERIZATION USING ABERROMETRY

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 406 days.

(21) Appl. No.: 18/475,372

(22) Filed: Sep. 27, 2023

(65) Prior Publication Data

US 2024/0099576 A1 Mar. 28, 2024

Related U.S. Application Data

(60) Provisional application No. 63/377,223, filed on Sep. 27, 2022.

(51) Int. Cl.
*A61B 3/10* (2006.01)
*A61B 3/00* (2006.01)
(Continued)

(52) U.S. Cl.
CPC .......... *A61B 3/1015* (2013.01); *A61B 3/0025* (2013.01); *A61B 3/102* (2013.01);
(Continued)

(58) Field of Classification Search
CPC ..... A61B 3/1015; A61B 3/0025; A61B 3/102; A61B 3/103; A61B 2560/02;
(Continued)

(56) References Cited

U.S. PATENT DOCUMENTS 3,780,979 A 12/1973 De Guillebon
4,357,088 A 11/1982 Pomerantzeff
(Continued)

FOREIGN PATENT DOCUMENTS

AU 2018274939 B2 6/2020
CN 210009227 U 2/2020
(Continued)

OTHER PUBLICATIONS

Adrian G.H. Podoleanu et al., Combined optical coherence tomograph and scanning laser ophthalmoscope mi nije dostupan besplatno., Electronics Letters, 34 (11), 1998.
Chi-Hung Lee, et al., Imaging vitreous floaters and cataracts with optical simulations, Optik, 194, 1-9, 2019.
Christy K. Sheehy et al., High-speed, image-based eye tracking with a scanning laser ophthalmoscope, Biomedical Optics Express, vol. 3, No. 10, 2012.
(Continued)

*Primary Examiner* — Mohammed A Hasan
(74) *Attorney, Agent, or Firm* — Patterson + Sheridan, LLP

(57) ABSTRACT

Particular embodiments include, by a computing device, receiving one or more wavefront elevation maps for a patient's eye and identifying one or more attributes of the one or more wavefront elevation maps corresponding to vitreous floaters. The one or more attributes may include localized spatial variation of the one or more wavefront elevation maps; temporal variation among a plurality of wavefront elevation maps; and depth information indicating scattering of light from within the vitreous of the patient's eye. A machine learning model may be trained and utilized to characterize vitreous floaters based on the one or more wavefront elevation maps and other patient data. The wavefront elevation maps may be measured using an aberrometer. The aberrometer may be integrated with a LIDAR system to estimate depth of scattered light. A common laser light source may be used for both the aberrometer and the LIDAR system.

16 Claims, 4 Drawing Sheets

(51) Int. Cl.

| | |
|---|---|
| ***A61B 3/103*** | (2006.01) |
| ***G01S 17/894*** | (2020.01) |
| ***G06T 7/00*** | (2017.01) |

(52) U.S. Cl.

CPC ............ *A61B 3/103* (2013.01); *G01S 17/894* (2020.01); *G06T 7/0016* (2013.01); *A61B 2560/02* (2013.01); *A61B 2560/04* (2013.01); *G06T 2207/30041* (2013.01)

(58) Field of Classification Search

CPC . A61B 2560/04; G01S 17/894; G06T 7/0016; G06T 2207/30041; A61F 9/00825; A61F 2009/00848; A61F 2009/00874

USPC ........................................................ 351/205

See application file for complete search history.

(56) References Cited

U.S. PATENT DOCUMENTS

| | | | |
|---|---|---|---|
| 5,312,396 | A | 5/1994 | Feld |
| 5,909,270 | A | 6/1999 | Moser |
| 6,142,630 | A | 11/2000 | Koester |
| 6,322,556 | B1 | 11/2001 | Gwon |
| 6,789,900 | B2 | 9/2004 | Van De Velde |
| 7,374,287 | B2 | 5/2008 | Van De Velde |
| 7,510,282 | B2 | 3/2009 | Ueno |
| 7,520,613 | B2 | 4/2009 | Saito et al. |
| 7,703,922 | B2 | 4/2010 | Van De Velde |
| 8,480,659 | B2 | 7/2013 | Frey et al. |
| 8,652,602 | B1 | 2/2014 | Dolla |
| 8,783,868 | B2 | 7/2014 | Qiu |
| 8,876,808 | B2 | 11/2014 | Feklistov et al. |
| 8,994,753 | B2 | 3/2015 | Nakano |
| 9,033,500 | B2 | 5/2015 | Utsunomiya |
| 9,603,519 | B2 | 3/2017 | Bor et al. |
| 9,675,243 | B2 | 6/2017 | Sasak et al. |
| 9,789,002 | B2 | 10/2017 | Van De Velde |
| 10,130,511 | B2 | 11/2018 | Dantus |
| 10,478,342 | B2 | 11/2019 | Dick |
| 10,555,835 | B2 | 2/2020 | Schuele et al. |
| 2007/0258094 | A1 | 11/2007 | Izatt et al. |
| 2007/0291277 | A1 | 12/2007 | Everett |
| 2009/0073384 | A1 | 3/2009 | Warden |
| 2009/0137989 | A1 | 5/2009 | Kataoka |
| 2009/0196477 | A1 | 8/2009 | Cense et al. |
| 2010/0123873 | A1 | 5/2010 | Raymond |
| 2010/0152847 | A1 | 6/2010 | Padrick |
| 2011/0077557 | A1 | 3/2011 | Wing et al. |
| 2012/0281235 | A1 | 11/2012 | Murata |
| 2013/0131652 | A1 | 5/2013 | Dick |
| 2013/0173029 | A1 | 7/2013 | Caldeira et al. |
| 2014/0058367 | A1 | 2/2014 | Dantus |
| 2014/0216468 | A1 | 8/2014 | Goldshleger |
| 2014/0257257 | A1 | 9/2014 | Grant et al. |
| 2014/0268036 | A1 | 9/2014 | Ketterling et al. |
| 2014/0276674 | A1 | 9/2014 | Lee |
| 2015/0190278 | A1 | 7/2015 | Gooding |
| 2015/0342782 | A1 | 12/2015 | Mordaunt |
| 2016/0058617 | A1 | 3/2016 | Luttrull et al. |
| 2016/0074214 | A1 | 3/2016 | Palanker et al. |
| 2016/0074221 | A1 | 3/2016 | Tassignon et al. |
| 2016/0166431 | A1 | 6/2016 | Vogler et al. |
| 2016/0227999 | A1 | 8/2016 | An et al. |
| 2016/0235588 | A1 | 8/2016 | Hart et al. |
| 2016/0256324 | A1 | 9/2016 | Suzuki |
| 2016/0278629 | A1 | 9/2016 | Schuele |
| 2016/0302969 | A1 | 10/2016 | Yamamoto |
| 2017/0181625 | A1 | 6/2017 | Kawakami et al. |
| 2017/0252213 | A1 | 9/2017 | Furuuchi et al. |
| 2017/0326003 | A1 | 11/2017 | Schuele et al. |
| 2018/0028354 | A1 | 2/2018 | Heeren |
| 2018/0028355 | A1 | 2/2018 | Raksi |
| 2018/0140257 | A1 | 5/2018 | Govindjee et al. |
| 2018/0206719 | A1 | 7/2018 | Adler et al. |
| 2018/0317767 | A1 | 11/2018 | Ryan |
| 2018/0353064 | A1 | 12/2018 | Soetikno et al. |
| 2018/0368915 | A1 | 12/2018 | Xia et al. |
| 2019/0076242 | A1* | 3/2019 | Pinto .................... A61F 2/1648 |
| 2019/0127034 | A1* | 5/2019 | Larson .................... G01S 17/08 |
| 2019/0159933 | A1 | 5/2019 | Romano et al. |
| 2019/0282403 | A1 | 9/2019 | Barrett et al. |
| 2019/0290124 | A1 | 9/2019 | Laforest et al. |
| 2019/0313903 | A1 | 10/2019 | Mckinnon |
| 2019/0365569 | A1 | 12/2019 | Skovgaard |
| 2020/0038241 | A1 | 2/2020 | Wang et al. |
| 2020/0060873 | A1 | 2/2020 | Heeren |
| 2020/0085292 | A1 | 3/2020 | Fukuma et al. |
| 2020/0129336 | A1 | 4/2020 | Schuele et al. |
| 2020/0130103 | A1 | 4/2020 | Choi |
| 2020/0192080 | A1 | 6/2020 | Karam |
| 2020/0196853 | A1 | 6/2020 | Van Hemert et al. |
| 2020/0273218 | A1* | 8/2020 | Camino ................ G16H 50/20 |
| 2020/0397289 | A1 | 12/2020 | Ralston |
| 2020/0400422 | A1 | 12/2020 | Ralston |
| 2021/0100450 | A1 | 4/2021 | Amma |
| 2021/0186753 | A1 | 6/2021 | Al-Qaisi et al. |
| 2021/0275009 | A1 | 9/2021 | Yates |
| 2021/0378507 | A1 | 12/2021 | Wallace |
| 2021/0386586 | A1 | 12/2021 | Bor |
| 2022/0012459 | A1 | 1/2022 | Schwiegerling |
| 2022/0031511 | A1 | 2/2022 | Charles |
| 2022/0225874 | A1* | 7/2022 | Nekrassov ............ G16H 50/50 |
| 2023/0157889 | A1 | 5/2023 | Bor |
| 2023/0301511 | A1* | 9/2023 | Tsukada ................... A61B 3/10 |

FOREIGN PATENT DOCUMENTS

| | | | |
|---|---|---|---|
| CN | 108371542 | B | 4/2020 |
| CN | 109196333 | B | 12/2020 |
| CN | 111281651 | B | 12/2020 |
| CN | 112862782 | A | 5/2021 |
| CN | 112587302 | B | 6/2021 |
| CN | 112587304 | B | 6/2021 |
| DE | 19705044 | A1 | 8/1998 |
| DE | 102019007147 | A1 | 4/2021 |
| DE | 102019007148 | A1 | 4/2021 |
| EP | 0770370 | A2 | 2/1997 |
| EP | 1212022 | B1 | 3/2005 |
| EP | 1563785 | A1 | 8/2005 |
| EP | 1638452 | B1 | 10/2006 |
| EP | 1838212 | A1 | 10/2007 |
| EP | 2144552 | A1 | 1/2010 |
| EP | 1928297 | B1 | 11/2010 |
| EP | 2459138 | A2 | 6/2012 |
| EP | 2525706 | A2 | 11/2012 |
| EP | 2898820 | A1 | 7/2015 |
| EP | 3061429 | A1 | 8/2016 |
| EP | 2890340 | B1 | 2/2017 |
| EP | 3459487 | A1 | 3/2019 |
| EP | 3501463 | A1 | 6/2019 |
| EP | 3636137 | A1 | 4/2020 |
| EP | 3861924 | A1 | 8/2021 |
| GB | 2469249 | A | 10/2010 |
| JP | 5767014 | B2 | 6/2015 |
| JP | 2017176558 | A | 10/2017 |
| JP | 6410468 | B2 | 10/2018 |
| JP | 2018196821 | A | 12/2018 |
| JP | 2018196822 | A | 12/2018 |
| JP | 2020022569 | A | 2/2020 |
| JP | 6736304 | B2 | 7/2020 |
| JP | 6839902 | B2 | 2/2021 |
| RU | 2661016 | C1 | 7/2018 |
| RU | 2692666 | C1 | 6/2019 |
| RU | 2695629 | C1 | 7/2019 |
| RU | 2710058 | C2 | 12/2019 |
| RU | 2726468 | C1 | 7/2020 |
| WO | 9958047 | A1 | 11/1999 |
| WO | 0137769 | A1 | 5/2001 |
| WO | 0195791 | A1 | 12/2001 |
| WO | 2007059189 | A2 | 5/2007 |
| WO | 2009033110 | A2 | 3/2009 |
| WO | 2009036104 | A2 | 3/2009 |
| WO | 2009039315 | A2 | 3/2009 |

(56) References Cited

FOREIGN PATENT DOCUMENTS

| | | | |
|---|---|---|---|
| WO | 2009059400 | A1 | 5/2009 |
| WO | 2010117386 | A1 | 10/2010 |
| WO | 2014053824 | A1 | 4/2014 |
| WO | 2015131135 | A1 | 9/2015 |
| WO | 2015171793 | A1 | 11/2015 |
| WO | 2016033590 | A1 | 3/2016 |
| WO | 2017062673 | A1 | 4/2017 |
| WO | 2017196306 | A1 | 11/2017 |
| WO | 2017205857 | A1 | 11/2017 |
| WO | 2020074532 | A1 | 4/2020 |
| WO | 2020180729 | A1 | 9/2020 |
| WO | 2020215359 | A1 | 10/2020 |
| WO | 2020216763 | A1 | 10/2020 |
| WO | 2020257711 | A1 | 12/2020 |
| WO | 2021023799 | A1 | 2/2021 |
| WO | 2021049243 | A1 | 3/2021 |
| WO | 2021066047 | A1 | 4/2021 |
| WO | 2021092211 | A1 | 5/2021 |
| WO | 2021183637 | A1 | 9/2021 |
| WO | 2022149028 | A1 | 7/2022 |
| WO | 2023089416 | A1 | 5/2023 |
| WO | 2023089459 | A1 | 5/2023 |
| WO | 2023097391 | A1 | 6/2023 |

OTHER PUBLICATIONS

D. H. Kelly, "Retinal Inhomogeneity. II. Spatial Summation," J. Opt. Soc. Am., pp. 114-119, vol. 1, No. 1 (Jan. 1984).
D. H. Kelly, "Retinal Inhomogeneity. III. Circular-Retina Theory," D.H. Kelly, J. Opt. Soc. Am., pp. 810-819, vol. 2, No. 6 (Jun. 1985).
D.H. Kelly, "Visual Processing of Moving Stimuli," J. Opt. Soc. Am., pp. 216-225, vol. 2, No. 2 (Feb. 1985).
D.H. Kelly,, "Motion and Vision. II. Stabilized Spatio-Temporal Threshold Surface," J. Opt. Soc. Am., pp. 1340-1349, vol. 69, No. 10 (Oct. 1979).
D.H.Kelly, "Retinal Inhomogeneity. I. Spatiotemporal Contrast Sensitivity," J. Opt. Sec. Am., pp. 107-113, vol. 1, No. 1 (Jan. 1984).
Mojana F. et al.. Observations by spectral-domain optical coherence tomography combined with simultaneous scanning laser ophthalmoscopy: imaging of the vitreous, American Journal of Ophthalmol. Apr. 2010; 149(4):641-650.
Nidek, Scanning Laser Ophthalmoscope Mirante SLO/OCT Mirante SLO, https://www.nidek-intl.com/product/ophthaloptom/diagnostic/dia_retina/mirante.htm.
Peter G. J. Barten, "Contrast Sensitivity of the Human Eye and its Effects on Image Quality," Chapter 3, pp. 27-40, Model for the spatial contrast sensitivity of the eye, (1999).
Pointer, J. S., & Hess, R. F. "The contrast sensitivity gradient across the human visual field: With emphasis on the low spatial frequency range,", R. F. Vision Research, 29(9), 1133-1151 (1989).
Sebag J et al., Vitreous and Vitreoretinal Interface, Ch. 21, 2015.
Sebag J., Vitreous and Vision Degrading Myodesopsia. Progress in Retinal and Eye Research Nov. 2020;79.
T Ivanova et al, Vitrectomy for primary symptomatic vitreous opacities: an evidence-based review, Eye (Lond) May 2016; 30(5):645-55.
Teri T Kleinberg et al., Vitreous substitutes: a comprehensive review, Survey of Ophthalmology, 56 (4), 2011.
Blake F. Webb, et al.; "Prevalence of vitreous floaters in a community sample of smartphone users"; International Journal of Ophthalmology; Jun. 18, 2013; pp. 402-405; 6(3); PMC/ US National Library of Medicine National Institutes of Health.
Chirag P. Shah, et al., YAG Laser Vitreolysis vs Sham YAG Vitreolysis for Symptomatic Vitreous Floaters a Randomized Clinical Trial, JAMA Ophthalmology, Sep. 2017, 918-923, 135-9.
Damodaran et al., "Digital micromirror device based ophthalmoscope with concentric circle scanning", vol. 8, No. 5, pp. 2766-2780, 2017, Biomedical Optics Express.
Ellex Website, Treatment Guidelines—Laser Floater Removal; 2016, Ellex Medical Pty Ltd. E&OE. VB0002E, downloaded Apr. 20, 2017.
Felix Sauvage et al.: "Photoablation of Human Vitreous Opacities by Light-Induced Vapor Nanobubbles", ACS Nano, vol. 13, No. 7, Jul. 9, 2019, pp. 8401-8416.
Fischer et al., "Scanning Laser Ophthalmoscopy (SLO)", In: Bille JF, editor. High Resolution Imaging in Microscopy and Ophthalmology: New Frontiers in Biomedical Optics [Internet], accessed on Jan. 30, 2023 from https://www.ncbi.nlm.nih.gov/books/NBK554043, Aug. 14, 2019, Springer.
Ginner et al., "Wide-Field OCT Angiography at 400 KHz Utilizing Spectral Splitting", Photonics, vol. 1, No. 4, pp. 369-379, Oct. 23, 2014.
Heidelberg Engineering GMBH, "Spectralis. Hardware Operating Instructions," Version 001, Aug. 2007.
Heidelberg Engineering, "Spectralis. Multimodal Imaging Platform Optimized for the Posterior Segment", accessed on Jan. 30, 2023 from https://business-lounge.heidelbergengineering.com/us/en/products/spectralis/spectralis/.
Hofer et al., "Dispersion encoded full range frequency domain optical coherence tomography", vol. 17, No. 1, pp. 7-24, Jan. 5, 2009, Optics Express, US.
Hofer et al., "Fast dispersion encoded full range optical coherence tomography for retinal imaging at 800 nm and 1060 nm", vol. 18, No. 5, pp. 4898-4919, Mar. 1, 2010, Optics Express.
Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.
Leitgeb et al., "Complex ambiguity-free Fourier domain optical coherence tomography through transverse scanning", vol. 32, pp. 3453-3455, 2007, Optics Letters.
Li et al., "DMD-based three-dimensional chromatic confocal microscopy", vol. 59, No. 14, pp. 4349-4356, 2020, Applied Optics.
Martial et al., "Programmable Illumination and High-Speed, Multi-Wavelength, Confocal Microscopy Using a Digital Micromirror", vol. 7, No. 8, e43942, Aug. 2012, PLOS ONE.
Michael J. Escuti, et al., "Geometric-Phase Holograms", Optics & Photonics News, pp. 22-29, Feb. 2016.
Milston Rebecca et al: "Vitreous floaters: Etiology, diagnostics, and management", Survey of Ophthalmology, vol. 61, No. 2, Mar. 1, 2016, pp. 211-227.
Nicusor Iftimia et al: "Hybrid retinal imaginer using line-scanning laser ophthalmoscopy and spectral domain optical coherence tomography", Optics Express, vol. 14, No. 26, Dec. 22, 2006.
Reece Bergstrom, et al., Vitreous Floaters, National Center for Biotechnology Information, May 21, 2020, 4 pages, Bookshelf ID NBK470420, StatPearls Publishing LLC, online.
Reznicek Lukas et al., "Wide-Field Megahertz OCT Imaging of Patients with Diabetic Retinopathy", Journal of Diabetes Research, 2015, 5 pages.
Ruggeri et al., "Imaging and full-length biometry of the eye during accommodation using spectral domain OCT with an optical switch", vol. 3, No. 7, pp. 1506-1520, Jul. 1, 2012, Biomedical Optics Express.
Sarunic et al., "Instantaneous complex conjugate resolved spectral domain and swept-source OCT using 3x3 fiber couplers", vol. 13, No. 3, pp. 957-967, Feb. 2005, Optics Express.
Shields et al., "Wide-angle Imaging of the Ocular Fundus", Review of the Ophthalmology, Feb. 15, 2003.
Singh, "Lasers Take Aim at Floaters", Ophthalmology Management, vol. 23, pp. 38, 40-42, 59, Jul. 1, 2019.
Singh, "Modern vitreolysis—YAG laser treatment now a real solution for the treatment of symptomatic floaters", Survey of Ophthalmology, vol. 65, No. 5, pp. 581-591, Mar. 3, 2020.
SunLED, NanoPoint-0201 Series LEDs, published Feb. 15, 2016, www.SunLEDusa.com.
Volk Optical, "Volk Idrees Mid-Vitreous Lens", accessed on Dec. 20, 2020 from https://www.volk.com/...s?pr_prod_strat=collection_fallback&pr_rec_pid=4513049018402&pr_ref_pid=4513048952866&pr_seq=uniform, Dec. 20, 2020.
Volk Optical, "Volk Singh Mid-Vitreous Lens", accessed on Dec. 20, 2020 from https://www.volk.com/products/singh-mid-vitreous-vitreous-slit-lamp-lens?_pos=3&_sid=b50c0674f&_ss=r, Dec. 20, 2020.

(56) References Cited

OTHER PUBLICATIONS

Wang et al., "In vivo full range complex Fourier domain optical coherence tomography", vol. 90, 054103, Jan. 30, 2007, Applied Physics Letters.
Wikipedia Encyclopedia, Floater, Wikipedia Encyclopedia, Mar. 29, 2021, online: https://en.wikipedia.org/wiki/rloater?wprov=sfti 1.
Wojtkowski et al., "Full range complex spectral optical coherence tomography technique in eye imaging", vol. 27, No. 16, pp. 1415-1417, 2002, Optics Letters.
Yasuno et al., "Simultaneous B—M-mode scanning method for real-time full-range Fourier domain optical coherence tomography", vol. 45, No. 8, pp. 1861-1865, 2006, Applied Optics.
Zhang et al., Removal of a mirror image and enhancement of the signal-to-noise ratio in Fourier-domain optical coherence tomography using an electro-optic phase modulator, vol. 30, No. 2, Jan. 15, 2005, Optics Letters.
Zhang Yunbo et al: "Parallel large-range scanning confocal microscope based on a digital micromirror device", Optik vol. 124, No. 13 (2013), Aug. 4, 2012, pp. 1585-1588.
Zhou et al., "Dual channel dual focus optical coherence tomography for imaging accommodation of the eye", vol. 17, No. 11, pp. 8947-8955, May 25, 2009, Optics Express.

* cited by examiner

Cluster per Patient Data 402

400

Train Machine Learning Models per Clusters 404

Select Machine Learning Model 406

Process Patient Data with Selected Machine Learning Model 408

VITREOUS FLOATER CHARACTERIZATION USING ABERROMETRY

BACKGROUND

The posterior chamber of the eye between the crystalline lens and the retina is occupied by a transparent gel known as the vitreous. Due to various causes, floaters may be present in the vitreous. Floaters are typically formed of clumps of cells and may have varying sizes and opacities. All eyes will have some floaters. However, the size, number, and opacity of floaters in the eye may be such that vision is significantly impaired. In that case, treatment may include removing the vitreous and replacing it with saline or a bubble made of gas or oil.

BRIEF SUMMARY

The present disclosure relates generally to a system for characterizing vitreous floaters using aberrometry.

In one aspect, a method performed by a computing device includes receiving one or more wavefront elevation maps for a patient's eye. The wavefront elevation maps are processed to identify one or more attributes of the one or more wavefront elevation maps corresponding to vitreous floaters. The one or more attributes may include localized spatial variation of the one or more wavefront elevation maps; temporal variation among a plurality of wavefront elevation maps; and depth information indicating scattering of light from within the vitreous of the patient's eye.

The following description and the related drawings set forth in detail certain illustrative features of one or more embodiments.

BRIEF DESCRIPTION OF THE DRAWINGS

The appended FIGURES depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
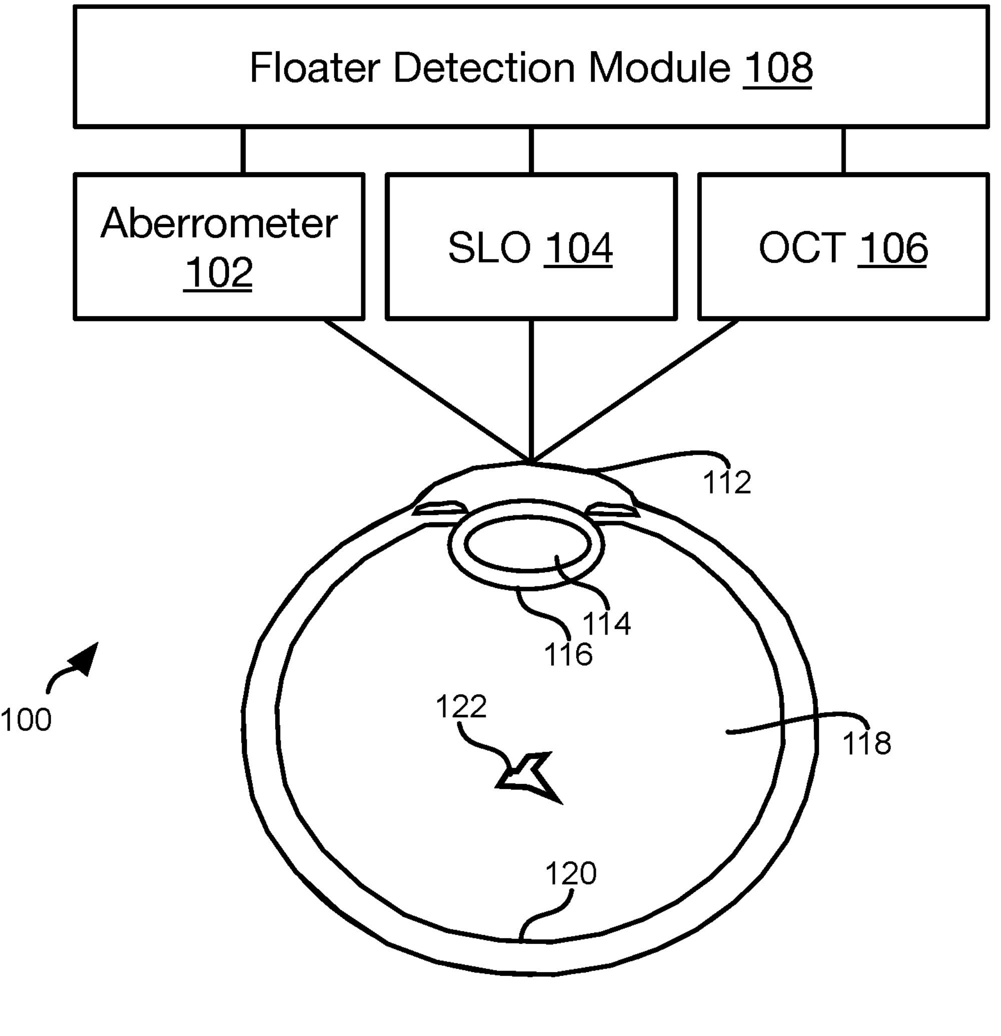
FIG. 1 is a schematic block diagram of a system for floater characterization using aberrometry, in accordance with certain embodiments.

Aberrometry is a relatively inexpensive approach for characterizing the refractive error of the eye. The output of an aberrometer is a wavefront elevation map in which the elevation at each point indicates a phase delay of a point on a planar wavefront passing through the cornea, lens, and vitreous of the eye to the retina. The wavefront elevation map may then be analyzed to characterize the refractive error of the eye. Using the approach described herein, an aberrometer is used to characterize the clinical significance of floaters in the eye.

A system 100 includes an aberrometer 102 configured to detect the refractive error of an eye 110. The aberrometer 102 may implement wavefront aberrometry that measures the propagation of a wavefront through the eye 110. In particular, the aberrometer 102 measures the propagation of the wavefront through the cornea 112, crystalline lens 114, capsulary bag 116, and vitreous 118 to the retina 120. For example, the aberrometer 102 may be implemented as or similar to the Optiwave Refractive Analysis (ORA) system by ALCON. The output of the aberrometer 102 is a wavefront elevation map comprising a two-dimensional array of values in which each value represents a point from which light was scattered and the elevation at each point represents the phase delay of a wavefront upon incident on that point. In some implementations, a two-dimensional array of amplitude of values such that for each index (e.g., X, Y coordinate) a phase and an amplitude value are stored indicating the phase delay and amplitude of light scattered from a point in space corresponding to the X, Y coordinate. The light beams emitted by the aberrometer 102 will be scattered by any floaters 122 within the vitreous. The degree of scattering will correspond to the number of floaters 122, the size of the floaters 122, and the opacity of the floaters 122.

The aberrometer 102 may be used alone to characterize floaters 122 or may be used in combination with other ophthalmic measurement devices such as a scanning laser ophthalmoscope (SLO) 104 and/or optical coherence tomography (OCT) device 106. For example, a SLO 104 and/or OCT device 106 may be used to confirm the presence of floaters 122 detected using the aberrometer 102 as described below and/or to precisely identify the locations of any detected floaters 122. In some implementations, the aberrometer 102, SLO 104, and OCT device 106 are contained within a same housing.

Figure 2:
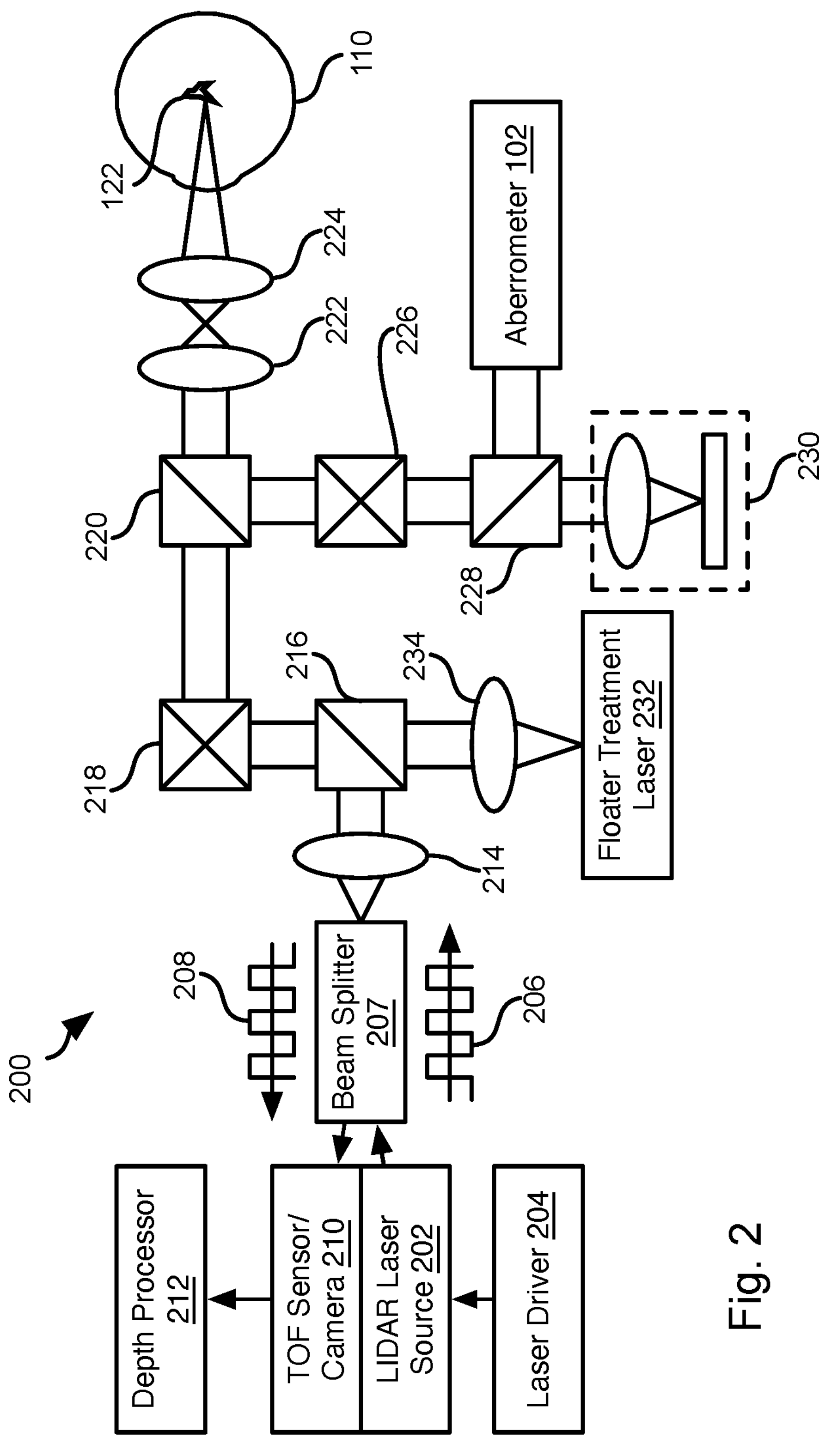
FIG. 2 is a schematic block diagram of a system for performing aberrometry along with depth measurement of scattered light, in accordance with certain embodiments.

Referring to FIG. 2, an aberrometer 102 may be used as part of the illustrated system 200 in order to detect floaters 122. The system 200 includes a light detection and ranging (LIDAR) laser source 202 controlled by a laser driver 204, which causes the LIDAR laser source 202 to emit a series of pulses 206 having a known period between pulses and duration of pulses. The pulses 206 are pass through a beam splitter 207 to the eye 110. Return pulses 208 including light reflected from the eye 110 pass through the beam splitter and a portion thereof is received by a time-of-flight (TOF) sensor/camera 210. TOF measurements from the TOF sensor/camera 210 are input to a depth processor 212, which interprets the TOF measurements to estimate depth of a point in the eye 110 that scattered the return pulses 208.

The pulses 206 may reach the eye 110 by passing through a collimating lens 402 and a dichroic mirror 216, which directs light from the collimating lens 402 onto a rotating mirror 218 rotating about one or two axes, such as a galvo scanner. Light reflected by the rotating mirror 218 is incident on a dichroic mirror 220. The portion of light transmitted through the dichroic mirror is incident on one or more objective lenses 222, 224 that focus the light output from the objective lenses onto the eye 110. Light scattered by the eye 110, including floaters 122 within the eye 110, returns through the objective lenses 222, 224, transmits through the dichroic mirror 220, is descanned by the rotating mirror 2187, is incident on dichroic mirror 216, passes through the lens 214, and is incident on the beam splitter 1010. A portion of the light scattered by the eye 110 is directed by the beam splitter 1010 onto the TOF sensor/camera 210.

A portion of the light scattered by the eye 110 is directed by the dichroic mirror 220 onto another rotating mirror 226, which may be rotatable about one or two axes and be implemented as a galvo mirror. The rotating mirror 226 descans the portion of the scattered light onto a dichroic mirror 228, which directs a portion of the descanned light onto the aberrometer 102. A portion of the descanned light is transmitted through the dichroic mirror onto a fixation target used to calibrate the TOF sensor/camera 210.

In the illustrated embodiment, a floater treatment laser 232 is also included. For example, light from the floater treatment laser 232 may pass through a collimating lens 234, through the dichroic mirror 216, onto the rotating mirror 218, which scans the light from the floater treatment laser 232 onto the eye 110 through the dichroic mirror 220 and objective lenses 222, 224 onto the eye 110. The floater treatment laser 232 may generate pulses of light focused on floaters 122 and having sufficient intensity to disintegrate floaters 122. The timing and depth of focus of pulses generated by the floater treatment laser 232 may be controlled using locations and depth of floaters 122 determined using the TOF sensor/camera 210 and depth processor 212. For example, a depth of focus of a treatment pulse from the floater treatment laser 232 may be selected using a depth estimate from the depth processor 212 and the treatment pulse may be emitted when the rotating mirror 218 is at the same position as when the pulse 206 was emitted that was used to obtain the depth estimate.

In the foregoing description, various beam splitters and dichroic mirrors are discussed. It shall be understood that the arrangements of elements as receiving transmitted or reflected light from a beam splitter or dichroic mirror may be reversed: a first element receiving transmitted light and a second element receiving reflected light from a beam splitter or dichroic mirror may be substituted with the first element receiving the reflected light and the second element receiving the transmitted light.

The system 200 uses the LIDAR laser source 202 to bounce low-power optical pulses off a target, i.e., the eye 110, and detecting the light reflected using the TOF sensor/camera 210. The TOF sensor/camera 210 captures time-stamped images. The depth processor 212 then calculates a time of flight based on the time-stamp and the known transmission time of each pulse 206. The distance to a structure that scattered light detected in an image may then be calculated using the speed of light. The distance may be combined with the known orientation of the rotating mirror 218 to obtain high resolution information in all three dimensions. In particular, for each pulse 208 received, the position of the rotating mirror 218 and distance estimate may be used to obtain a three dimensional coordinate of a point in the eye 110 that scattered the pulse 208. The amplitude of each pulse 208 indicates the reflectivity (and correspondingly the opacity) of the point in the eye. Accordingly, a point cloud results in which each point has a three dimensional coordinate and a reflectivity.

The LIDAR laser source 202 can emit hundreds of thousands of pulses 206 per second. Some of the light from each pulse may be reflected from a floater 122 returned to the TOF sensor/camera 210. The point cloud would therefore include points corresponding to pulses 206 reflected from the floater 122. Due to the small size of floaters 122, a resolution of less than 100 mm is desired, which may be obtained using a pulse generation frequency of more than 350 MHz.

The aberrometer 102 measures wavefront aberrations of the eye, such as by using reflected light from the same pulses 206. The floaters 122 inside the eye, which may be moving, act as disturbance to the optical path. The floaters 122 cause fluctuations in the index of refraction along the beam path and scatter light, both of which add noise to the wavefront measurement. By performing TOF and wavefront measurements simultaneously, the wavefront deviations along different sections of the beam path through the vitreous 118 may be correlated to the location of a structure, e.g., floater 122, that caused the wavefront deviation. The aberrometer 102 may also provide a continuous sampling of the pupil size. The 3D measurements may further be used with tomographic reconstruction software to generate refractive map of vitreous 118. Such a refractive map indicates the locations, size, and opacity of floaters 122. Once floaters 122 have been identified as described above, the clinical significance of the floaters may be determined using the following parameters. For example, the distance between the floaters and retina, the area and darkness of the shadow caused by the floaters on retain etc. Magnitude of disturbance of the floaters can be estimated using local variance (or roughness) of the waveform profile.

Figures 3, 4:
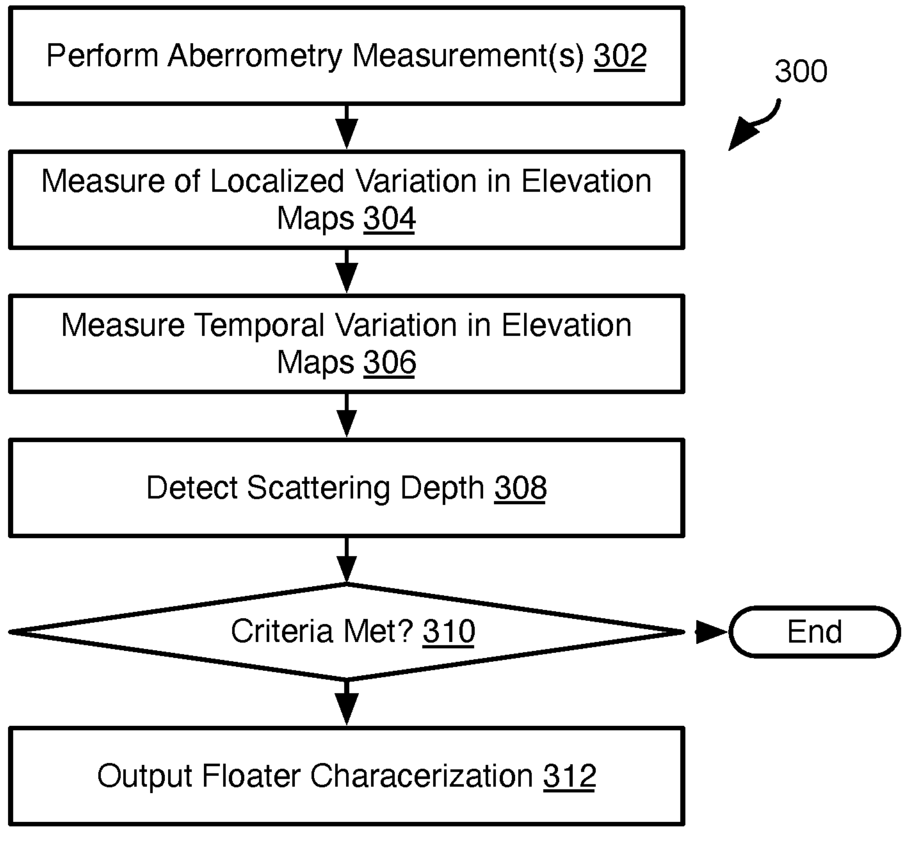
FIG. 3 is a process flow diagram of a method for characterizing floaters using aberrometry, in accordance with certain embodiments.
FIG. 4 is a process flow diagram of a method for training a machine learning model to characterize floaters using aberrometry data, in accordance with certain embodiments.

FIG. 3 illustrates a method 300 for characterizing floaters using aberrometry. The method 300 may be performed by the floater detection module 108 using wavefront elevation maps received from the aberrometer 102. The method 300 may be performed with or without the system 200 as described in greater detail below. The method 300 identifies attributes of one or more wavefront elevation maps that may correspond to vitreous floaters in order to determine the clinical significance of the vitreous floaters. These attributes include some or all of localized spatial variation, temporal variation, and depth values as described in greater detail below.

The method 300 includes performing, at step 302, aberrometry measurements of the patient's eye 110. Step 302 may include simply performing multiple aberrometry measurements at a fixed or variable period. Step 302 may include performing aberrometry measurements simultaneously with distance measurements as described above with respect to the system 200. The result of each aberrometry measurement is a wavefront elevation map. The wavefront elevation map may be viewed as an image in which each pixel position (X, Y coordinate) has an elevation value associated therewith indicating a phase delay. As noted above, each X, Y coordinate may also have an amplitude value. The wavefront elevation map will have a generally circular shape corresponding to the pupil of the eye 110.

The method 300 may include measuring, at step 304, localized variation in each wavefront elevation map. Refractive error in the eye 110 will result in the wavefront elevation map being non-planar. The presence of cataracts likewise results in scattering that is uniformly distributed. However, the scattering caused by a floater 122 may result in localized elevation variation in a wavefront elevation map that is distinguishable from elevation variation caused by refractive error. Localized variation may be measured in various ways. For example, a sliding-window two-dimensional spatial Fourier transform may be calculated for each elevation map or for discrete regions at some or all points (e.g., X, Y coordinates) in each selected elevation map for one or both of phase and amplitude values. For example, the discrete regions may have height and width that is between 0.05 and 0.15 times the diameter of the wavefront elevation map. Frequencies above a frequency threshold and with a magnitude above a magnitude threshold in a Fourier transform may be deemed to correspond to vitreous floaters. The output of step 304 may therefore be a function of the magnitude (e.g., average, maximum, integral) of the portion of the two-dimensional Fourier transform above a threshold frequency. There are many other methods to measure and analyze local variation of the wavefront (phase elevation map), such as Landmark-based geometric morphometrics, principal components analysis, as well as analyses of global variational properties of morphological features, such as morphological integration etc. Also, wavefronts acquired over a period of time can be analyzed to obtain the de-correlation of wavefront change/fluctuation over time. The de-correlation of the wavefront change/fluctuation over time can be analyzed to determine which area of the phase elevation map fluctuates the most due to the floaters.

The method 300 may include measuring, at step 306, temporal variation among the wavefront elevation maps. Floaters 122 may move within the vitreous 118 such that any scattering caused thereby is different in wavefront elevation maps captured at different times. In contrast, variation in wavefront elevation maps caused by cataracts or refractive error should not change over time. Step 306 may be accompanied by performing eye tracking and compensating for eye movement when performing aberrometry measurements at step 302. In this manner, movement in the locations of regions of localized variation can more reasonably be attributed to movement of floaters 122 rather than eye movement. Measuring temporal variation may be performed in various ways. For example, a Z coordinate may be defined as an index assigned to each elevation map, with the indexes corresponding to the temporal ordering in which the wavefront elevation maps were obtained at step 302. Temporal variation may therefore be obtained by characterizing variation along the Z axis. For example, for a given X, Y coordinate a volume may be defined including the X, Y coordinates and the range of possible Z coordinates. A three-dimensional Fourier transform of this volume may therefore be calculated for this volume at step 302 for one or both of phase and amplitude values. As an alternative, an alternative volume may be defined as the Fourier transforms from step 304 for all Z coordinates. Values of either three-dimensional Fourier transform at frequencies above a frequency threshold and with a magnitude above a magnitude threshold may be deemed to correspond to vitreous floaters. The output of step 306 may therefore be a function of the magnitude (e.g., average, maximum, integral) of the three-dimensional Fourier transform above a threshold frequency.

In the case where the system 200 is used, the method 300 may further include measuring, at step 308, the scattering depth, such as using TOF measurements as described above. For example, scattering found at a depth that is between the capsular bag 116 and the retina 120, i.e., the vitreous 118, may be deemed to correspond to vitreous floaters 122. Step 308 may be omitted in order to characterize floaters using only an aberrometer 102. Step 308 may include measuring the reflectivity of points within the vitreous 118 and generating a score based thereon, e.g. a sum or weighted sum of the reflectivity of points within the vitreous 118.

Step 308 may also be performed using another imaging modality such an SLO 104 or OCT device 106. An SLO 104 is capable of measuring the distance of a floater to the retina by focusing on the retina and then shifting the SLO focus to the floater. The distance to the retina can be measured by converting focus diopter change to a distance. An OCT device 106 is also capable of measuring distance of floater to ocular structures in a like manner. Either a long-range OCT can be used to detect the full vitreous in one scan or a shorter-range OCT can be used with multiple scans to detect floaters in the vitreous. The distance to the retina can be measured with proper calibration of the OCT system and by converting pixel locations to distance measurements.

The method 300 may include evaluating, at step 310, whether a clinical criteria has been met. For example, some or all of the localized variation as measured at step 304, the temporal variation as measured at step 306, and the scattering depth as measured at step 308 may be evaluated with respect to individual thresholds or combined (e.g., summed, weighted and summed, multiplied, etc.) and compared to a single threshold. Where some or all of the individual thresholds are exceeded or the single threshold is exceeded, the patient's eye 110 may be deemed to have clinically significant floaters such that laser ablation or vitrectomy is needed. Alternatively or additionally, where the criteria of step 310 are met, other actions may be performed, such as scanning the eye 110 using another imaging modality, such as an SLO 104 or OCT device 106 in order to map the size and location of the vitreous floaters.

If the clinical criteria is found to have been met, then a characterization of vitreous floaters may be output at step 312, which may include any of the information evaluated at step 310 (localized variation as measured at step 304, the temporal variation as measured at step 306, and/or the scattering depth as measured at step 308).

FIG. 4 illustrates a method 400 that may be used to characterize vitreous floaters. The method 400 may be used with, or in place of, the method 300. For example, the method 400 may be used at step 310 to determine whether clinically significant floaters are present.

The method 400 may include clustering, at step 402, training data entries. Training data entries may be clustered using k-means clustering, k nearest neighbor, or other clustering technique. Training entries may include, as inputs, patient data including such information as demographic data (age, sex, ethnicity) and comorbidities (cataracts, retinal disease). The inputs of each entry further includes aberrometry data in the form of a single wavefront elevation map or a series of wavefront elevation maps obtained over time as described above with respect to step 302. Each wavefront elevation map may include one or both of phase and amplitude values. Each training data entry may further include, as a desired output, a metric of floaters detected in the eye of the patient, such as obtained using an SLO or OCT device. The metric of floaters may include a human generated estimate of clinical significance, a score indicating combined reflectivity of points within the vitreous 118, or some other metric of floaters. Clustering at step 402 may include performing multiple linear regression with the inputs of the training data entries as explanatory data and the desired output of the training data entries as the response variable.

The training data entries of each cluster may then be used to train a machine learning model for each cluster such that each cluster has a corresponding machine learning model. Each machine learning model may be trained to output, for a given set of inputs, an estimate of clinical significance of vitreous floaters. Each machine learning model may be any machine learning model known in the art such as a deep neural network (DNN), convolution neural network (CNN), multiple polynomial regression (MPR) ($2^{nd}$ order, $3^{rd}$ order, or higher) model, support vector regression model (SVM), or SVM radial bias function (SVM-RBF).

During utilization, patient data (demographic data, co-morbidities, wavefront elevation map(s)) may be processed to select, at step 406, a corresponding cluster, such as using the same clustering technique used at step 402 or a different clustering technique. The patient data may then be processed, at step 408, using the machine learning model for the selected cluster to obtain a predicted clinical significance of floaters in the patient's eye. The utilization of steps 406 and 408 may be performed using a different computing device than is used to perform steps 402 and 404.

The method 400 is exemplary only. For example, clustering 402 may be omitted and a single machine learning model trained to predict clinical significance of floaters using the training patient data. The training patient data used for each entry may include less than or more than the items of data listed above. For example, comorbidities may be omitted and the machine learning model trained to predict clinical significance of floaters without a priori knowledge of co-morbidities, such as cataracts or retinal disease. In particular, cataracts will scatter light used to perform aberrometry and the machine learning model (or models) may be trained to account for this phenomenon.

Figure 5:
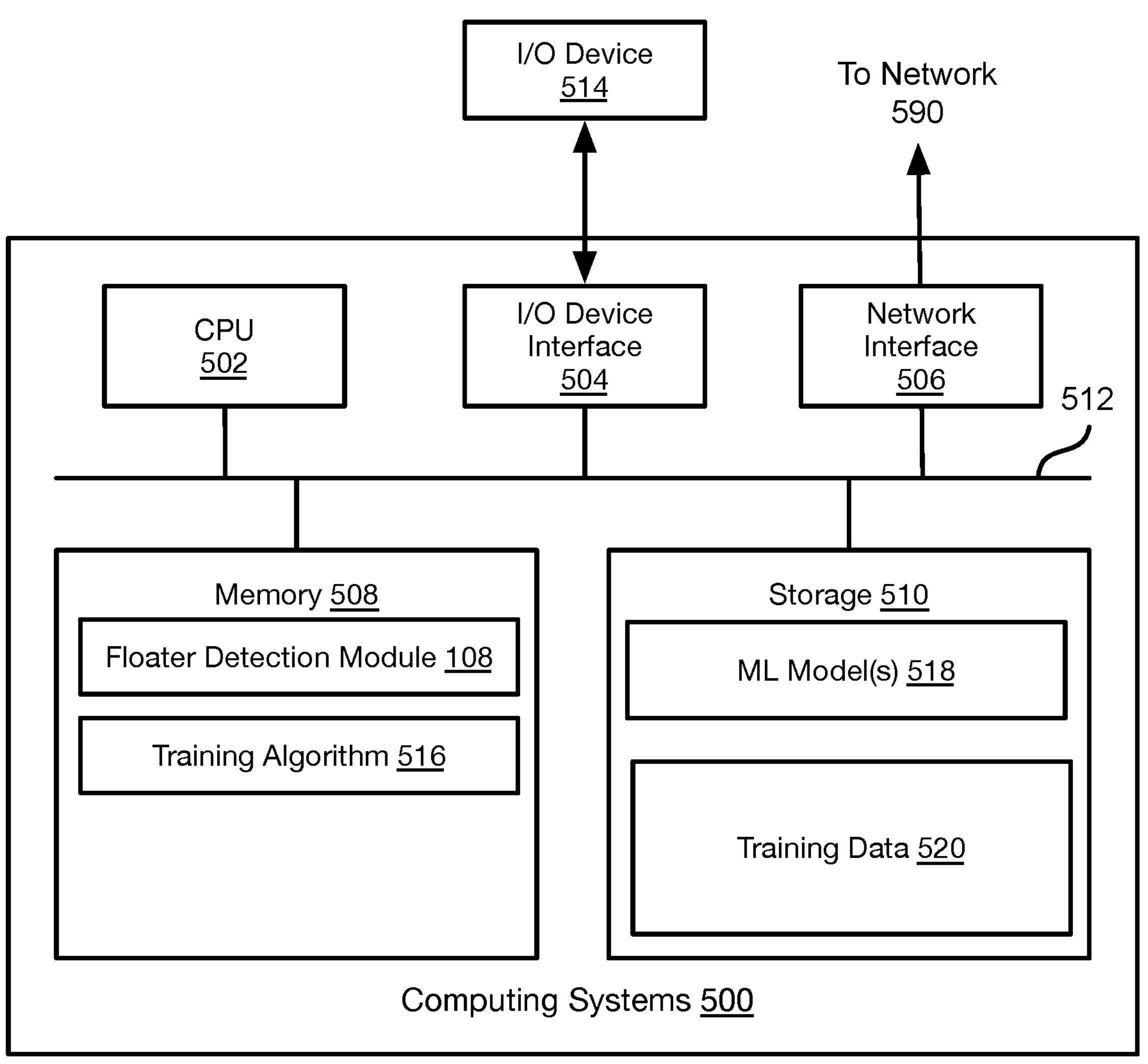
FIG. 5 illustrates an example computing device that implements, at least partly, one or more functionalities of creating and presenting a primary treatment plan and one or more backup plans.

FIG. 5 illustrates an example computing system 500 that implements, at least partly, one or more functionalities described, such as one or both of the method 300, the method 400, and processing described above with respect to the system 200. The computing system 500 may be integrated with an imaging device, such as an aberrometer 102, or be a separate computing device receiving images of a patient's eye from the imaging device.

As shown, computing system 500 includes a central processing unit (CPU) 502, one or more I/O device interfaces 504, which may allow for the connection of various I/O devices 514 (e.g., keyboards, displays, mouse devices, pen input, etc.) to computing system 500, network interface 506 through which computing system 500 is connected to network 590 (which may be a local network, an intranet, the internet, or any other group of computing systems communicatively connected to each other, as described in relation to FIG. 1), a memory 508, storage 510, and an interconnect 512.

In cases where computing system 500 is an imaging system, such as a digital microscope, computing system 500 may further include one or more optical components for obtaining ophthalmic imaging of a patient's eye as well as any other components known to one of ordinary skill in the art. In cases where computing system 500 is a surgical microscope, computing system 500 may further include many other components known to one of ordinary skill in the art to perform the ophthalmic surgeries described herein as known to one of ordinary skill in the art.

CPU 502 may retrieve and execute programming instructions stored in the memory 508. Similarly, CPU 502 may retrieve and store application data residing in the memory 508. The interconnect 512 transmits programming instructions and application data, among CPU 502, I/O device interface 504, network interface 506, memory 508, and storage 510. CPU 502 is included to be representative of a single CPU, multiple CPUs, a single CPU having multiple processing cores, and the like.

Memory 508 is representative of a volatile memory, such as a random access memory, and/or a nonvolatile memory, such as nonvolatile random access memory, phase change random access memory, or the like. As shown, memory 508 may store executable code that is executable by the CPU 502 to implement some or all of the floater detection module 108, the processing described above with respect to the system 200, and the method 300. The memory 508 may additionally or alternatively store executable code implementing a training algorithm 516 used during steps 402 and 404 of the method 400.

Storage 510 may be non-volatile memory, such as a disk drive, solid state drive, or a collection of storage devices distributed across multiple storage systems. Storage 510 may optionally store a machine learning model 518, or multiple machine learning models 518, trained as described above with respect to FIG. 4. Where the computing system 500 is used for training the machine learning model(s) 514, the storage 510 may further store training data 520 including a plurality of training data entries including patient data as described above with respect to FIG. 4.

Additional Considerations

The preceding description is provided to enable any person skilled in the art to practice the various embodiments described herein. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in FIG- URES, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. An ophthalmic system for guiding ophthalmic surgery comprising:

an aberrometer;

one or more processing devices;

one or more memory devices coupled to the one or more processing devices and storing executable code that, when executed by the one or more processing devices, causes the one or more processing devices to:

receive one or more wavefront elevation maps for a patient's eye from the aberrometer; and identify one or more attributes of the one or more wavefront elevation maps corresponding to vitreous floaters;

wherein the one or more wavefront elevation maps comprise a plurality of wavefront elevation maps captured at different times and the one or more attributes include temporal variation among the plurality of wavefront elevation maps.

2. The ophthalmic system of claim 1, wherein the one or more attributes include localized spatial variation of the one or more wavefront elevation maps.

3. The ophthalmic system of claim 1, wherein the one or more wavefront elevation maps comprise the plurality of wavefront elevation maps captured at different times and the one or more attributes include temporal variation among the plurality of wavefront elevation maps and localized spatial variation of the plurality of wavefront elevation maps.

4. The ophthalmic system of claim 1, wherein the aberrometer is an Optiwave Refractive Analysis (ORA) system.

5. The ophthalmic system of claim 1, further comprising:

a light distancing and ranging (LIDAR) system combined with the aberrometer and configured to capture depth information simultaneously with the one or more wavefront elevation maps;

wherein the one or more attributes include the depth information.

6. The ophthalmic system of claim 5, wherein the one or more attributes include whether the depth information indicates scattering within a vitreous of the patient's eye.

7. The ophthalmic system of claim 5, wherein the aberrometer and the LIDAR system have a common laser light source and a common scanning mirror.

8. The ophthalmic system of claim 1, wherein the executable code that, when executed by the one or more processing devices, further causes the one or more processing devices to identify the one or more attributes of the one or more wavefront elevation maps corresponding to the vitreous floaters by processing the one or more wavefront elevation maps with a machine learning model.

9. A method for characterizing vitreous floaters comprising:

measuring, by an aberrometer, a patient's eye to obtain one or more wavefront elevation maps;

receiving, by a computing device, the one or more wavefront elevation maps; and identifying, by the computing device, one or more attributes of the one or more wavefront elevation maps corresponding to vitreous floaters;

wherein the one or more wavefront elevation maps comprise a plurality of wavefront elevation maps captured at different times and the one or more attributes include temporal variation among the plurality of wavefront elevation maps.

10. The method of claim 9, wherein the one or more attributes include localized spatial variation of the one or more wavefront elevation maps.

11. The method of claim 9, wherein the one or more wavefront elevation maps comprise the plurality of wavefront elevation maps captured at different times and the one or more attributes include temporal variation among the plurality of wavefront elevation maps and localized spatial variation of the plurality of wavefront elevation maps.

12. The method of claim 9, wherein the aberrometer is an Optiwave Refractive Analysis (ORA) system.

13. The method of claim 9, wherein:

a light distancing and ranging (LIDAR) system is combined with the aberrometer and is configured to capture depth information simultaneously with the one or more wavefront elevation maps; and the one or more attributes include the depth information.

14. The method of claim 13, wherein the one or more attributes include whether the depth information indicates scattering within a vitreous of the patient's eye.

15. The method of claim 13, wherein the aberrometer and the LIDAR system have a common laser light source and a common scanning mirror.

16. The method of claim 9, wherein identifying the one or more attributes of the one or more wavefront elevation maps corresponding to the vitreous floaters comprises processing the one or more wavefront elevation maps with a machine learning model.

* * * * *